United States Patent [19]
Mauze et al.

[11] Patent Number: 5,720,650
[45] Date of Patent: Feb. 24, 1998

[54] GAS ANALYZER WITH ARRANGEMENT FOR SPRAY-CLEANING OPTICAL ELEMENT

[75] Inventors: Ganapati R. Mauze; George W. Hopkins, II, both of Sunnyvale; Tad Decatur Simons, Palo Alto, all of Calif.

[73] Assignee: Hewlett-Packard Company, Palo Alto, Calif.

[21] Appl. No.: 801,108

[22] Filed: Feb. 13, 1997

Related U.S. Application Data

[63] Continuation of Ser. No. 505,942, Jul. 24, 1995, abandoned.

[51] Int. Cl.⁶ .................................................. B24C 3/00
[52] U.S. Cl. ................................... 451/75; 451/39
[58] Field of Search ................................ 451/39, 41, 76, 451/53, 42, 75

[56] References Cited

U.S. PATENT DOCUMENTS

| | | | |
|---|---|---|---|
| 4,977,910 | 12/1990 | Miyahara et al. | 134/7 |
| 5,001,873 | 3/1991 | Rufin | 451/39 |
| 5,062,898 | 11/1991 | McDermott et al. | 134/7 |
| 5,107,764 | 4/1992 | Gasparrini | 101/425 |
| 5,153,671 | 10/1992 | Miles | 356/301 |
| 5,209,028 | 5/1993 | McDermott | 51/426 |
| 5,294,261 | 3/1994 | McDermott | 134/7 |
| 5,315,793 | 5/1994 | Peterson et al. | |
| 5,341,206 | 8/1994 | Pittaro et al. | 356/301 |
| 5,365,699 | 11/1994 | Armstrong et al. | 451/7 |
| 5,390,450 | 2/1995 | Goenka | 451/39 |
| 5,405,283 | 4/1995 | Goenka | 451/39 |

FOREIGN PATENT DOCUMENTS

| | | |
|---|---|---|
| 0112498A2 | 7/1984 | European Pat. Off. |
| 0662367A1 | 7/1995 | European Pat. Off. |
| 3538313A1 | 4/1986 | Germany. |

OTHER PUBLICATIONS

Hughes Aircraft Company, "Eliminate CFC Cleaning with Eco-Snow", 1991, 1993, G200257–01–G200257–29.

Laurence C. Archibald, et al., "The Cold Jet Process . . . ", Particles on Surfaces, Plenum Press, NY 1991, pp. 257–269.

M.W. Lewis, "Contamination Control . . . ", Society of Vacuum Coaters, (1992) pp. 411–413.

*Primary Examiner*—James G. Smith
*Assistant Examiner*—Derris H. Banks
*Attorney, Agent, or Firm*—Philip S. Yip

[57] ABSTRACT

A gas analysis apparatus for analysis of sample gas wherein the apparatus has a mechanism for cleaning optical elements such as reflectors and windows in the apparatus is provided. The gas analysis apparatus includes a light source for emitting light, a body having an isolated cavity in which the light emitted by the light source propagates, a detector for analyzing light scattered by the sample gas in the isolated cavity, and a spraying system connected to the body to spray a sublimable substance. The isolated cavity has one or more optical elements each with a surface. The spray of the sublimable substance is directed onto such a surface for in situ removal of contaminants. The body has a sample inlet port for introducing the sample gas into the cavity and an outlet port for venting gas from the cavity.

20 Claims, 5 Drawing Sheets

GAS ANALYZER WITH ARRANGEMENT FOR SPRAY-CLEANING OPTICAL ELEMENT

This is a continuation of application Ser. No. 08/505,942 filed on Jul. 24, 1995, now abandoned.

FIELD OF THE INVENTION

The present invention relates to a gas analyzer for analyzing a sample gas and a method of using and cleaning such a gas analyzer. More particularly, the present invention relates to a gas analyzer as well as the method of using and cleaning such a gas analyzer, which includes optical elements that can become fouled by contaminants in the sample gas such that the optical elements require cleaning periodically.

BACKGROUND

Raman light scattering has been used for analyzing gas samples successfully. In this method, when monochromatic light, typically generated initially from a laser, is used to irradiate a gas sample that contains many different types of gas molecules, the monochromatic light causes the gas molecules in the gas sample to excite and emit light of frequencies different from the incident light. Detection and analysis of the frequency changes of the scattered light from the incident light provide information on the identity and quantity of the components in the sample gas. For example, Raman light scattering has been employed successfully to analyze gas samples from patients' breaths, such as in determining the level of anesthesia during surgery.

To produce effective Raman light scattering, an adequate amount of light must be available for exciting the gas samples. However, gas samples often contain contaminants, which can include organic components and particulate matters. Such contaminants can foul the surfaces of optical elements in the gas analyzer. For example, in the case where the gas sampling cell (or cavity) is located within the resonant cavity of a laser, optical elements such as reflector (e.g., mirror), Brewster window, and the like may be in direct contact with the gas samples. After repeated use, the contaminants in the gas samples may deposit on the surfaces of the optical elements, such as the reflectors and windows, to reduce the amplitude of the exiting laser light.

For example, the optical elements in a gas analyzer used for analyzing the breaths of a human patient during surgery may be fouled by contaminants such as particulate matters, proteins, and other organic substances. After an optical element has been fouled to an unacceptable degree, the gas analyzer should be cleaned. In the past, the gas analyzer is opened by hand and wiped with a swab or a pad containing a solvent, such as acetone, to remove the contaminants. However, the light scattering elements and surfaces in such gas analyzers are generally small and delicate. Repeated opening and closing of the housing, as well as cleaning of the optical elements by wiping, may damage the optical elements or cause them to be misaligned.

To help prevent contaminants from accumulating on optical elements in the gas analysis system used for analyzing respiratory gas samples, U.S. Pat. No. 5,153,671 (Miles) discloses a gas analysis system having two buffer gas inlet ports, one on each end of a gas analysis cell for introducing a flow of buffer gas into the cell. The flow of buffer gas acts to confine the gas sample within the analysis chamber to reduce adverse effects that occur when the gas samples contact the optical elements. However, this method of reducing the contact of the gas samples with the optical elements may not completely eliminate contaminants from accumulating thereon and periodic cleaning may still be needed. Furthermore, this design is complex and the buffering gas may dilute the sample gas in the analysis cell.

In the printing industry, sprays of a particular material obtained by cooling a liquid or gas for use in cleaning has been disclosed. For example, U.S. Pat. No. 5,107,764 (Gasparrini) discloses an apparatus for cleaning printing press components such as a rotating blanket cylinder of an offset printing press with carbon dioxide snow or pellets. The snow or pellets are conveyed by a stream of air under pressure to a moving nozzle to be directed to a target that requires cleaning.

U.S. Pat. No. 5,294,261 (McDermott et al.) discloses a method for removing contaminating particles from a microelectronic surface using an impinging stream of an aerosol containing at least substantially solid argon or nitrogen particles. The solid particles are formed by expanding a pressurized liquid of argon or a gaseous and/or liquid nitrogen-containing stream.

Hughes Company has marketed ECO-SNOW systems using carbon dioxide snow for cleaning automobile bodies, disk drive parts, sun shields, valves, and the Hubble Space Telescope. In these systems, a jet of carbon dioxide snow is directed to the cleaning target by a hand-held cleaning wand.

However, it has not been shown or suggested that a spray of or solid particles of carbon dioxide or other substances can be used for cleaning optical elements in gas analyzers.

SUMMARY OF THE INVENTION

The present invention provides a gas analysis apparatus for analysis of sample gas wherein the apparatus has a mechanism for cleaning optical elements such as reflectors and windows in the apparatus. The gas analysis apparatus includes a light source (e.g., a laser) for emitting light a body having an isolated cavity in which the light emitted by the light source propagates, a detector for analyzing light scattered by the sample gas in the isolated cavity, a container containing a pressurized substance that is gaseous under ambient conditions, and a spraying system affixed in the cavity which sprays the substance as a sublimable substance. The body has a sample inlet port for introducing the sample gas into the cavity and an outlet port for venting gas from the cavity. The isolated cavity has one or more optical elements (e.g., mirror, window) each with a reflective surface or a surface adapted for light transmission. On such a surface is directed the spray of sublimable substance (e.g., carbon dioxide "snow") for in situ removal of contaminants from that surface. As used herein, the term "sublimable substance" refers to a substance that is sprayed out of the spraying system onto the optical elements in solid form but is stable in its gaseous form in the ambient (or environmental) condition (e.g., hospital room or laboratory) in the isolated cavity so that the solid sublimes without going through the liquid phase. The term "isolated cavity" refers to a cavity that is substantially enclosed such that environmental gases have no free access to the cavity except through inlet ports or outlet ports. Further, such inlet and outlet ports can be controlled with valves to result in a completely enclosed cavity. The term "in situ removal" refers to the removal of contaminants from an optical element with a system that is affixed inside the isolated cavity such that the contaminants can be removed without opening the body to expose the optical element to the environment.

The present invention also provides a method of using a gas analysis apparatus which has a light source for emitting light, a body having an isolated cavity in which the light emitted by the light source propagates, and a detector for analyzing light scattered by the gas. The body has a sample inlet port for introducing a sample gas into the isolated cavity and an outlet port for venting gas from the cavity. The cavity has one or more optical elements. Each optical element has a reflective surface or a surface adapted for light transmission such as a mirror or a window. The method includes admitting a sample gas for analysis into the isolated cavity, analyzing the sample gas by irradiating the gas sample with light emitted from the light source and detecting the light scattered by the gas, and spraying a sublimable substance on the surface of the optical element to remove contaminants.

The present invention further provides a method for cleaning an optical element with a reflective surface or a surface adapted for light transmission in an isolated cavity. The method includes spraying a sublimable substance onto the surface of the optical element with an in situ nozzle in the isolated cavity, subliming the sublimable substance, and venting from the isolated cavity the sublimed sublimable substance and the contaminants removed from the optical element.

The gas analysis apparatus of the present invention can be used advantageously to analyze sample gases that contain contaminants, such as particulate matters, organic matters, proteins, and the like, because the spraying system of the present invention can be used to remove such contaminants effectively and efficiently from optical elements in the apparatus. Applicable analytical techniques that can be used in a gas analysis apparatus of the present invention include, but are not limited to, Raman scattering, Rayleigh scattering, fluorescence, phosphorescence, and the like. In such gas analysis apparatuses (e.g., utilizing Raman light scattering technology), the cleanliness as well as the alignment of the optical elements, such as the reflectors in the resonant cavity of the laser, is important for efficient use of laser energy. For example, the reduction of reflectivity of the reflector by contaminants will cause resonating energy loss and therefore less Raman light scattering. The misalignment of the reflector or shifting of position of the light emitter or the reflectors will cause the light beam emitted by the light emitter to be misdirected, again lowering the amount of laser energy available for producing desirable Raman light scattering. The present invention can be used to clean the optical elements without opening the body of the gas analyzer, thereby reducing the risk of misaligning the optical elements.

Although solid argon and carbon dioxide particles have been used for cleaning before, such prior art uses are very different from the apparatuses and methods of the present invention. In cleaning microelectronics, there is no need to monitor the extent of fouling. In the cleaning of printing equipment, automobile body, etc., the extent of "fouling" can be easily determined because the fouled surfaces are readily inspectable. To clean gas analyzers, one challenge is to clean the optical element intermittently only (only when cleaning is needed) so as not to wear out the optical elements unnecessarily. Another challenge is to clean the optical element while maintaining alignment of the optical system in an isolated cavity. In the preferred embodiment in which a resonant cavity of a laser is used for confining the sample gas, the high light intensity in the resonant cavity renders it particularly suitable for gas analysis. However, in this embodiment, the cleanliness and correct alignment of the optical system is particularly important for obtaining accurate result. The present invention meets these challenges and provides a technique that allows monitoring and in situ cleaning in even small gas analyzers.

Using the present invention also obviates the need to wipe by hand the optical elements with a swab (or pad) having an ultra-clean solvent (such as acetone, isopropanol, trichloroethane, chlorofluorocarbons (CFC), and the like) as traditionally done in cleaning gas analyzers. Wiping by hand often leaves behind traces of the solvent or even bits of the swab (or pad) on the surface of the optical element. After the solvent evaporates, traces of contaminants dissolved in the solvent may be left on the optical element. Furthermore, such solvents may adversely affect the environment. The optical elements in gas analyzers can be quite small (e.g., a resonant cavity having a 0.1 cm diameter lumen including a reflector of as small as 0.5 cm across the reflective surface). Traditional types of carbon dioxide snow jet cleaning devices such as the wand type marketed by Hughes Company are bulky and are difficult to use in a small, confined area, such as in the analysis cell (i.e., the isolated cavity) of a gas analyzer. Further, such devices require skilled labor to carefully control the positioning and release of the sprays.

In the present invention, the use of in situ contaminants removal in the isolated cavity also prevents environmental water vapor in air from condensing, freezing, and being carded along by the spray to impinge on the surface of the optical element. It has been found that such water and ice particles will reduce the efficiency of cleaning. Ice particles may melt when they impart on the optical element and absorb heat. The water and ice may block some of the sublimable substance from having direct access to the surface of the optical element. In an isolated cavity such as that of the present invention, because the cavity is isolated, the mount of atmospheric water vapor present is minimal and any water vapor can be flushed out rapidly by the gas in the spray and by the gas formed by sublimation of the sublimable substance.

It has been found that using carbon dioxide ($CO_2$) particles ("snow") to remove contaminants from optical elements in an isolated cavity further has the advantage that the calibration steps can be simplified. Carbon dioxide was found to be a suitable gas for use as a standard gas in the calibration of the gas analyzer. Carbon dioxide is a normal by-product of human respiration and an important measurement quantity for analysis of respiratory gases. With its known Raman spectra, measurement with 100% carbon dioxide in the isolated cavity gives amplitude calibration of the spectral lines. After the optical element in the gas analyzer has been cleaned with a spray of particulate carbon dioxide according to the present invention, the residual gaseous carbon dioxide in the isolated cavity caused by the sublimation of the particulate carbon dioxide can be used for calibration.

In the present invention, using a plenum or other means for producing bursts of a specific amount of the sublimable substance results in reproducible cleaning of the optical elements because the amount of sublimable substance used does not vary significantly among different bursts. In this way, the optical surface can be cleaned reliably without producing excessive wear on the optical surface or releasing an excessive amount of the sublimable substance into the environment or the isolated cavity. Further, such a system is particularly adaptable for automatic control. For example, a monitor can be used to monitor the light loss caused by absorption and scattering on the optical element. When a threshold amount of light loss is detected, the monitor can transmit a signal to activate the spraying system to spray a burst of the sublimable substance onto the surface of the optical element to clean the surface, thereby restoring the reflectivity or transmittance of the optical element. In this way, an entirely automatic system can be utilized to clean intermittently the optical element to maintain acceptable performance of the gas analyzer.

BRIEF DESCRIPTION OF THE DRAWING

The following figures which show the embodiments of the present invention are included to better illustrate the gas analyzer of the present invention. In these figures, wherein like numerals represent like features in the several views and structures are not drawn to scale.

DETAILED DESCRIPTION OF THE PREFERRED EMBODIMENT

Figure 1:
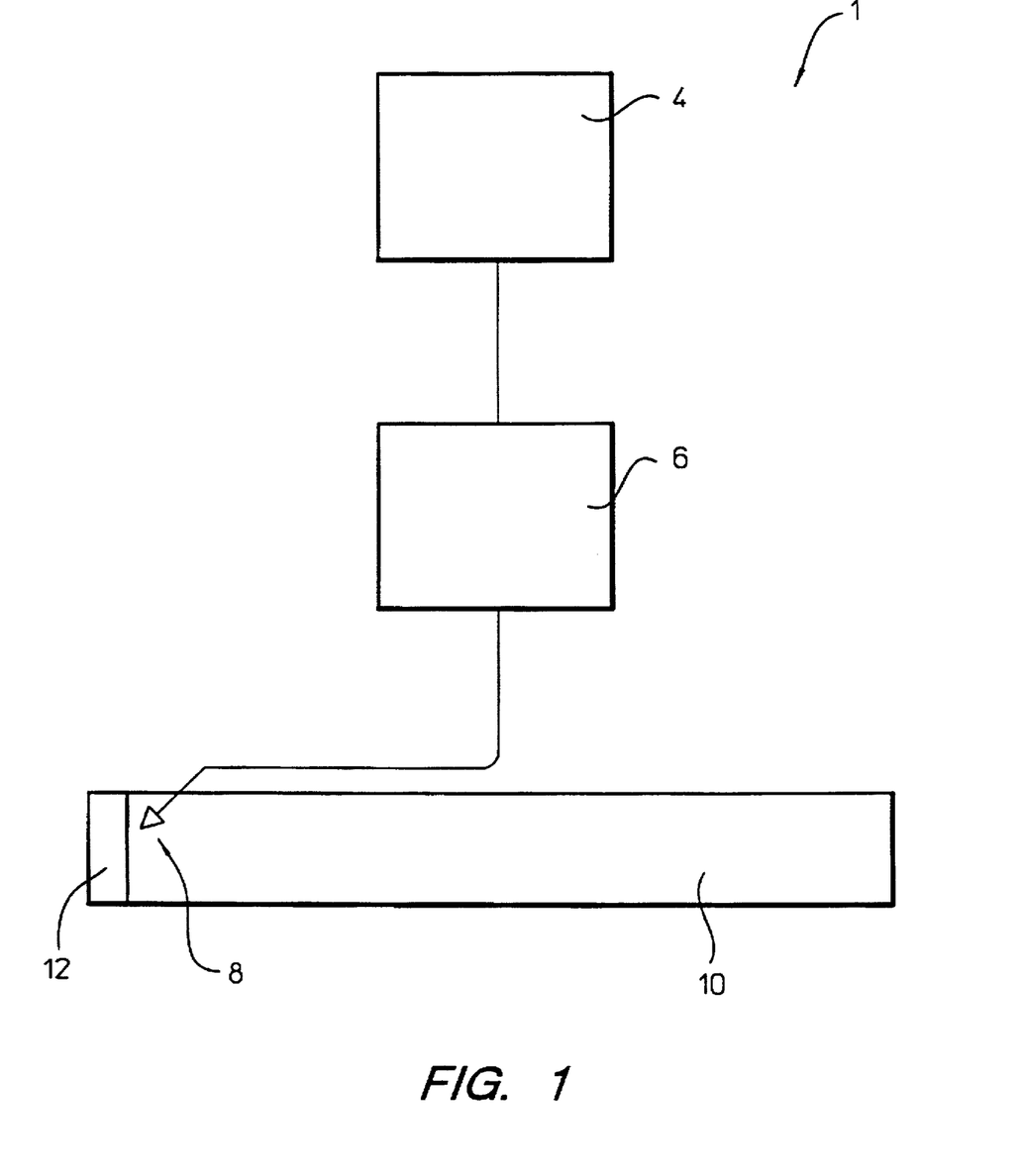
FIG. 1 is a schematic representation of an embodiment of the gas analysis apparatus of the present invention.

FIG. 1 shows a schematic representation of an embodiment of the gas analysis apparatus (or gas analyzer) of the present invention that has an arrangement for spray cleaning of an optical element in the gas analysis apparatus. In this embodiment, the gas analysis apparatus 1 has a source 4 of a substance to be sprayed as a sublimable substance for cleaning the optical element. A mechanism 6 transfers the substance to a spray outlet 8 (such as a nozzle). The gas analysis apparatus 1 has an isolated cavity 10 which can confine a sample gas for analysis. A light source (not shown in the drawing in FIG. 1 for the sake of clarity) irradiates the sample gas in the isolated cavity. The light emitted by the light source is transmitted to an optical element 12 in the gas analysis apparatus 1. The spray outlet 8 is positioned to emit a spray including a sublimable substance onto the surface of the optical element 12 for removing contaminants therefrom.

Figure 2:
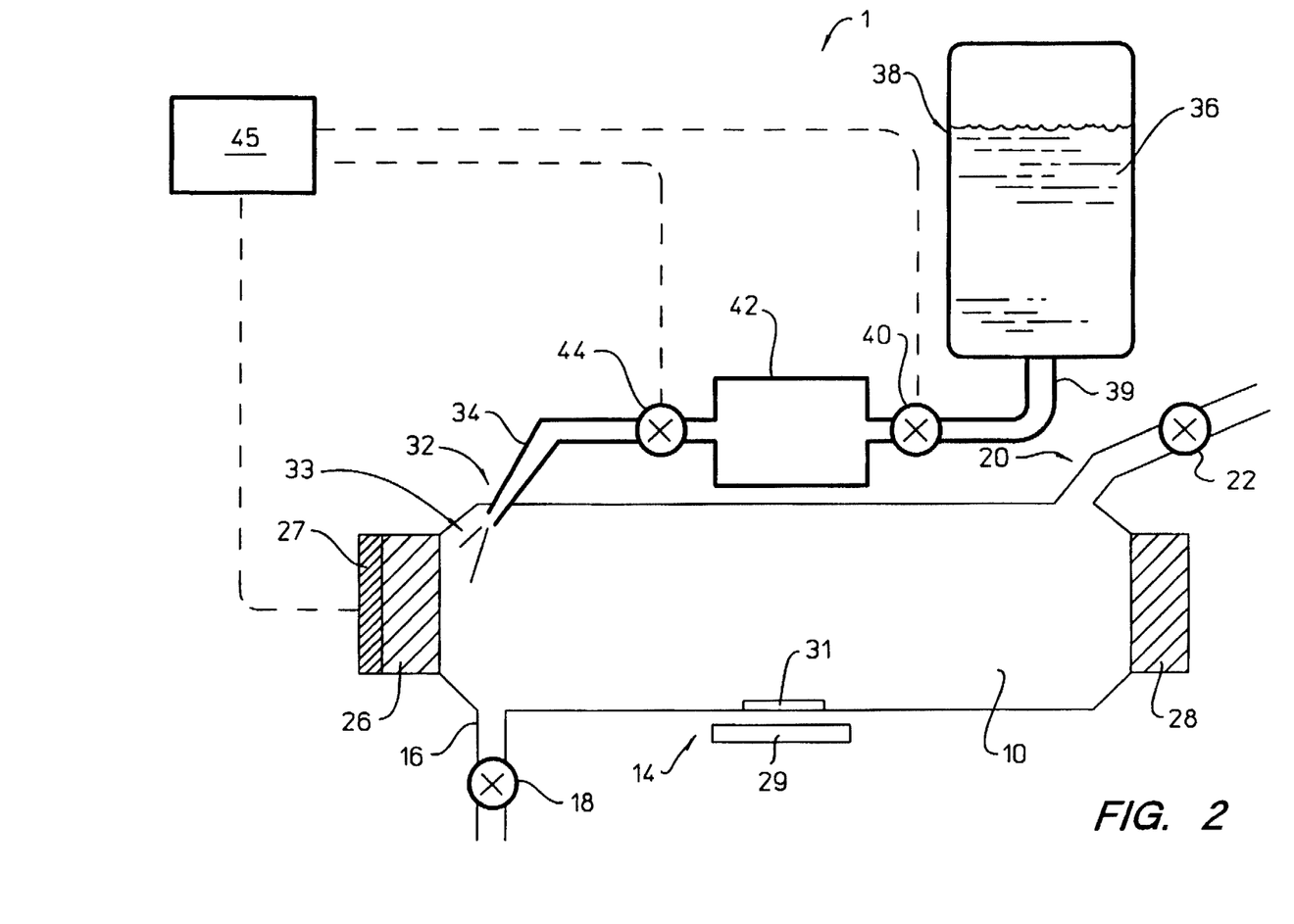
FIG. 2 is a schematic presentation of an embodiment of the present invention showing more details of the embodiment of FIG. 1.

In FIG. 2, which illustrates an embodiment of the present invention, the gas analysis apparatus 1 has a light source (not shown in FIG. 2 so as to show details of the other structures better) for emitting light. Preferably, the light source is the gain medium (or light emitter) such as a plasma discharge tube or laser diode of a laser. The gas analysis apparatus 1 has a body (or housing) 14 which includes an isolated cavity 10. The isolated cavity 10 is enclosable, for example, by closing inlet and outlet ports, such that a sample gas can be confined in the isolated cavity for analysis.

The body 14 of the gas analysis apparatus has a sample inlet port 16 for admission of the sample gas into the isolated cavity 10. The sample inlet port 16 can be controlled by a sample inlet valve 18 for isolating the isolated cavity 10 from the source of the sample gas. An outlet port 20 with an outlet valve 22 can be used for venting the gas in the isolated cavity. Preferably, the sample inlet port and the outlet port are positioned at opposite ends of the isolated cavity 10 (which is typically a linear structure). In this way, the dead space in the isolated cavity 10 is minimized so that a fresh sample of the sample gas can be introduced efficiently to flush out the old sample from the isolated cavity.

Figure 3:
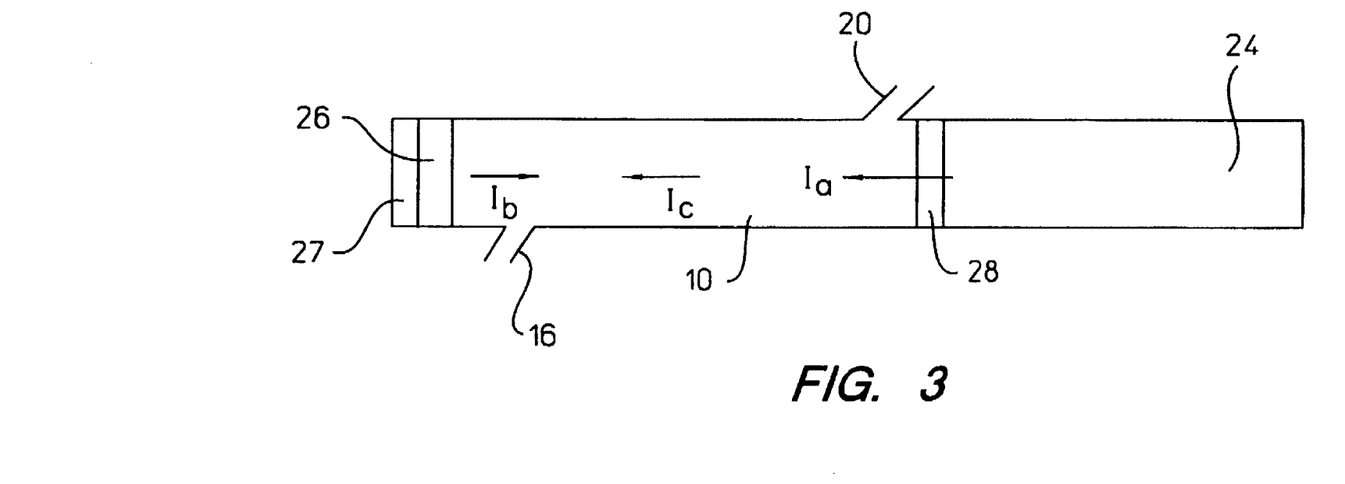
FIG. 3 is a schematic representation of the resonant cavity and the gain medium of the laser used in the gas analyzer of FIG. 2.
Figure 4:
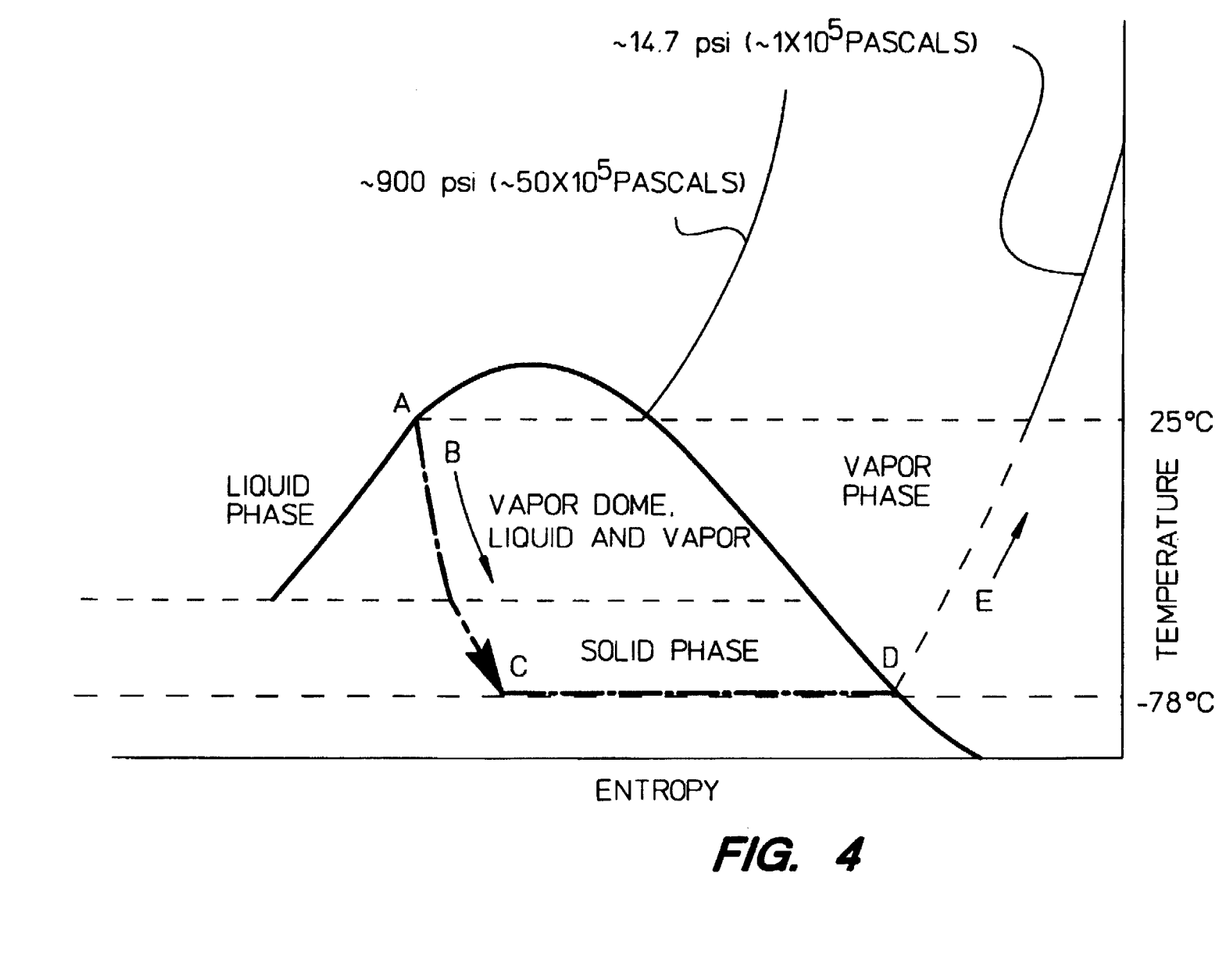
FIG. 4 is a graphical representation of the state diagram of carbon dioxide.
Figure 5:
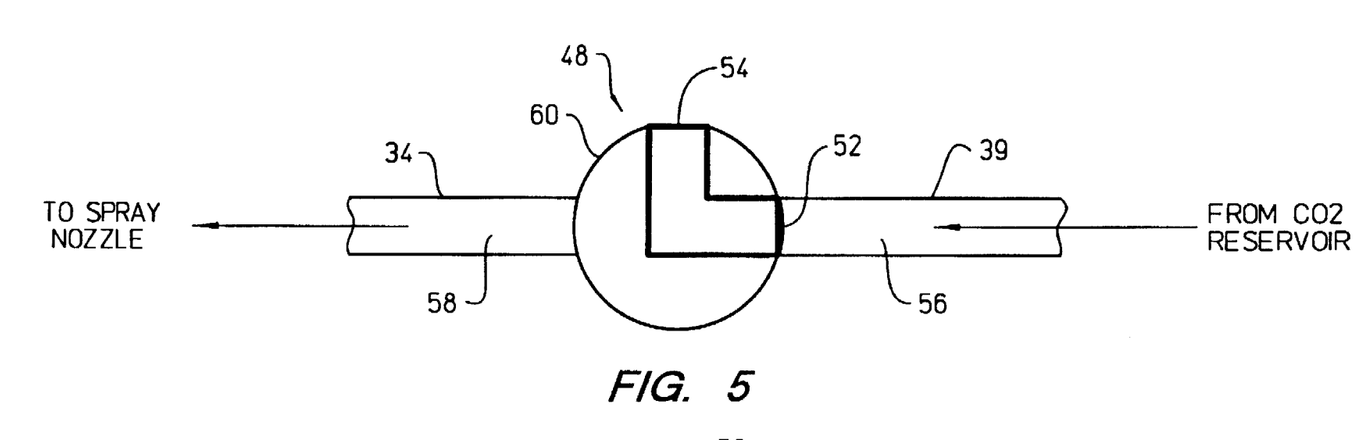
FIG. 5 is a schematic representation of the top view of a valve that can be used for dispensing a specific amount of the substance to be sprayed in a gas analyzer of the present invention, the valve being shown in a position to fill a chamber in the valve.
Figure 6:
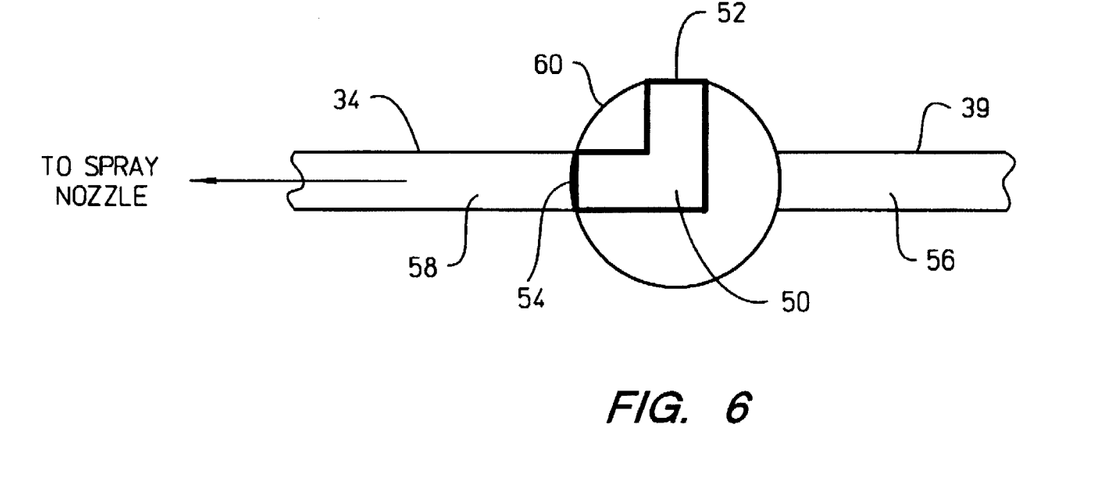
FIG. 6 is a schematic representation of the top view of the valve of FIG. 5 after the valve has been rotated to a different orientation to spray the sublimable substance from the chamber in the valve.
Figure 7:
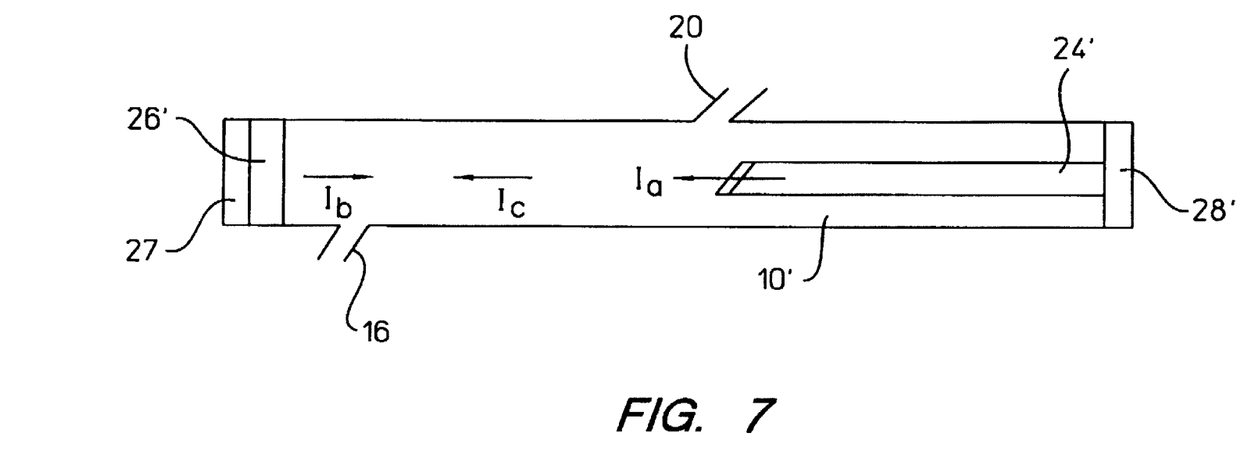
FIG. 7 is a schematic representation of another embodiment of the resonant cavity and the gain medium of a laser that can be used in the gas analysis apparatus of the present invention.

In FIG. 3, which shows in schematic representation the isolated cavity and the laser used in the embodiment of FIG. 2, the laser has a gain medium 24 external to isolated cavity 10 which also functions as the resonant cavity of the laser. The resonant cavity (i.e., the isolated cavity 10) has a first reflector 26 and a second reflector 28 respectively at its two ends. Laser light is transmitted (represented by Ia) from the gain medium 24, through the reflector 28 into the isolated cavity 10). Laser light is reflected by the reflectors 26 and 28 in the resonant cavity 10. The reflected light beams are represented by Ib and Ic. The reflectors 26, 28 are preferably dielectric mirrors made with glass having a dielectric coating such that laser light Ia from the gain medium 24 can be transmitted through reflector 28 into the resonant cavity and that a small amount of light will be transmitted through reflector 26 and be detected by detector 27.

The dimensions of the resonant cavity are such that the light beam transmitted into the resonant cavity from the gain medium resonates between the first and second reflectors 26, 28. In this way, the light beam propagates within the resonant cavity and interacts with the sample gas that is confined therein. The excitation of the atoms in the sample gas by the light results in Raman light scattering. The Raman scattering radiation is detected by a detector 29 (as shown in FIG. 2), which is preferably positioned lateral (i.e., offset from the axis of the resonant cavity) and external to the isolated cavity at a location appropriate for intercepting the Raman scattered light. The Raman scattered light that is detected by the detector 29 exits the isolated cavity through a window 31 on the body 14 that confines the sample gas. The technique for Raman light scattering as well as detection and analysis of such scattered light is well known in the art (e.g., as disclosed in U.S. Pat. No. 5,153,671 (Miles), whose disclosure related to the method and apparatus for producing, detecting, and analyzing of Raman light scattering in the analysis of gas samples is incorporated by reference herein).

The body 14, which defines the isolated cavity, is connected to a spraying system for removing contaminants from the reflector 26. The spraying system preferably includes a nozzle 32 that is affixed to the body inside the isolated cavity 10. The orientation of the nozzle 32 is such that a jet of spray 33 can be directed onto the surface of the reflector 26 to clean the desired area when desired by the emission of a spray from the nozzle. Such cleaning can be done intermittently after a predetermined period of analysis or when a threshold amount of resonating light loss at the reflector 26 by accumulated contaminants has been reached.

The nozzle 32 is connected by means of a conduit 34 for fluid communication with a supply of the substance to be sprayed. Preferably, the supply is a pressurized liquid 36 stored in a reservoir 38, for example, a steel tank. The reservoir 38 is preferably connected by means of a conduit 39 to a valve 40 connected to a plenum (or chamber) 42 which can be used for storing a specific volume of the liquid to be sprayed through the nozzle 32. A plenum outlet valve 44 connects the plenum 42 to conduit 34 such that when the plenum inlet valve 40 is closed and the plenum outlet valve 44 is opened the pressure inside the plenum 42 forces the liquid therein to exit the nozzle 32 as a spray. This can be done when contaminants are to be removed from the reflector 26.

In operation for cleaning the reflector 26, the plenum 42 is fast filled with the liquid 36, for example, by gravity, by closing plenum outlet valve 44 and then opening plenum inlet valve 40. Plenum inlet valve 40 can then be closed to confine a specific amount of the liquid 36 in the plenum 42. When it is determined that reflector 26 needs to be cleaned, the plenum outlet valve can be opened to force the liquid through conduit 34 to exit the nozzle 32. Preferably, before the spray is emitted into the isolated cavity 10, the sample inlet valve 18 is closed and the outlet valve 22 is opened to vent the gas from the isolated cavity 14. Preferably, during spraying, the pressure of the gas in the isolated cavity is about atmospheric pressure (i.e., about 76 cm of mercury at sea level) such that as the substance 36 exits nozzle 32 it expands and cools. Part of the gas forms flake-like particles that have the appearance of snow as a whole.

Preferably, the substance 36 is carbon dioxide ($CO_2$). Carbon dioxide can be stored in the reservoir 38 at room temperature under a pressure of about $57\times10^5$ Pascals (i.e., 830 psig) or more. In this condition, it is a liquid. When it is depressurized suddenly, for example, by allowing to exit from a nozzle to expand adiabatically to a pressure of about atmospheric pressure, solid carbon dioxide is formed. However, $CO_2$ can be stored at lower pressure as a gas as well. It can be used as long as adequate amount of "snow" can be formed by adiabatic decompression. Based on the present disclosure, a person skilled in the art would be able to determine the pressure and amount of $CO_2$ to be used for cleaning a particular surface on an optical element.

Referring to FIG. 4, which shows the state diagram of carbon dioxide. Point A represents the state of the liquid carbon dioxide in the plenum before being discharged through the nozzle. As the plenum outlet valve 44 is opened, allowing the carbon dioxide to emerge as a jet (or a spray) into the isolated cavity 10, the carbon dioxide expands (corresponding to line B in FIG. 4) and cools. The carbon dioxide undergoes a phase change and solidifies near minus 78° C. at about atmospheric pressure (represented by about point C in FIG. 4). The particulate carbon dioxide impacts on the surface of the optical element (i.e., reflector 26) to remove contaminants therefrom. The momentum of the particulate carbon dioxide results in a scrubbing effect for removing contaminants. Further, the expansion of carbon dioxide from solid to gas results in "microexplosions," which produces a flow of gas that carries contaminants from the surface. However, the "snowy" consistency of the particles allows the surface of the optical element to be cleaned without being scratched, thereby preserving the smoothness of the surface. The spray can also contain or transiently produce carbon dioxide in liquid form. Such liquid carbon dioxide can assist in dissolving some of the organic components in the contaminants. The carbon dioxide particle absorbs energy from its environment and sublimes (at point D in FIG. 4). The vaporized carbon dioxide gradually warms to the temperature of the environment (e.g., the ambient temperature in a laboratory is typically about 25° C.) along line E.

Using the plenum 42, the plenum inlet valve 40, and plenum outlet valve 44, bursts of spray of particulate carbon dioxide can be directed at an optical element (such as reflector 26) such that repeatable doses can be sprayed. The size of the dose can be varied to produce the best result by adjusting either the pressure of liquid 36 or the volume of the plenum 42. Also, if desired, an excess amount of carbon dioxide can be sprayed such that after sublimation and equilibrating to an appropriate temperature, the carbon dioxide gas in the isolated cavity can be used as a standard for calibration. As an alternative to the plenum with associating inlet and outlet valves 40, 44, a single valve as shown in FIG. 5 can be used.

As shown in FIG. 5, a valve 48 can be connected to the reservoir 38 and to the nozzle 32 respectively by conduits 39, 34. The valve 48 has a chamber 50 having two openings 52, 54. The size of the chamber is selected such that the amount of the liquid carbon dioxide that can be stored therein is suitable for providing a burst of spray adequate to remove contaminants from the surface of the optical element 26 to which the spray is directed. In operation, to fill the chamber 50 with liquid carbon dioxide, the valve 48 is rotated such that opening 52 of the valve faces the lumen 56 of the conduit 39 to allow liquid carbon dioxide to enter the chamber 50 therefrom. At the same lime, the opening 56 of the valve 48 is sealed by a part of the body of the valve 60.

When contaminants are to be removed from the surface of the optical element (e.g., the reflector 26), the valve 48 is rotated such that the opening 54 of the chamber 50 faces lumen 58 of the conduit 34 and the opening 54 of the chamber is sealed by the body of the valve. In this position, the fluid in the chamber 50 can expand through the lumen 58 of the conduit 34 and be expelled through the nozzle 32 into the isolated cavity 10. In this way, only one valve needs to be activated to provide a burst of spray from the nozzle for cleaning contaminants from the optical element. The size of the bursts can be reproduced reliably because a defined volume is emitted into the chamber and repeatable doses of substantially equal amount can be sprayed.

As an alternative to the embodiment shown in FIG. 3, an embodiment of the present invention in which the gain medium is within the resonant cavity, as shown in FIG. 7, can also be used. Such a laser and resonant cavity arrangement, as well as the laser and resonant cavity arrangement of FIG. 3, are commonly known in the art. For example, U.S. Pat. No. 5,153,671 discloses a laser-resonant cavity arrangement in which a plasma discharge tube is positioned inside a resonant cavity. Such an arrangement can be used in the gas analysis apparatus of the present invention and the mechanism for jet-spray-cleaning the surface of an optical element in the resonant cavity can be incorporated into such an arrangement.

In FIG. 7, the resonant cavity is defined at its two ends by reflectors 26' and 28'. A gain medium 24' is located inside the resonant cavity 10'. In one end of the gain medium light Ia is emitted to the isolated cavity through a Brewster window. Light is transmitted to the reflector 26' and propagates within the resonant cavity by reflecting off the reflectors 26', 28'. The reflected light beams are represented by Ib and Ic.

A monitoring system (e.g., including a detector 27 as shown in FIG. 2) can be incorporated into the embodiments of FIGS. 3 and 7 for monitoring the resonating light loss at any of the optical elements. When light falls on an optical element that transmits light, such as a dielectric mirror or a window, the accumulation of contaminants on the optical element scatters the incident light and reduces the amount of light transmitted through the optical element. Thus, the amount of light transmitted through the optical element (e.g., reflector 26) and detected (e.g., by detector 27) is inversely related to the amount contaminants on the optical element.

Due to the resonating characteristics of light in the resonant cavity, the ring-down time of light in the resonant cavity is significantly affected by the amount of contaminants on the optical elements. If the gain medium is turned off for a short period of time (e.g., a few microseconds), the amount of light that is reflected at the reflectors will decrease over time as it is dissipated by scattering from the contaminants and by transmission through the reflectors. This "ring-down time" corresponding to the decay of the light energy (i.e., resonating light loss) in multiple reflection off the reflectors is an indication of the cleanliness of the optical elements. The less the light energy impinging on the reflector, the less is the light transmitted therethrough. Thus, by monitoring the light transmitted through an optical element (e.g., reflector 26), the ring-down time, and hence the cleanliness of the optical element, can be gauged. For example, after turning off the gain medium, the energy stored in the resonating cavity is monitored by detecting the light energy transmitted out of the cavity with a photodetector, such as a photoelectric cell and an oscilloscope, as a function of time. From the profile of energy decay the Q (i.e., quality) factor, which is the ratio of energy stored to the energy lost per cycle of oscillation, can be measured. Such techniques and apparatuses for measuring ring-down time and determining the Q factor in a laser are well known in the art. A threshold level of cleanliness is selected based on the Q factor desired. The pressure of impact and amount of "snow" needed to clean the surface will depend on the extent of fouling (i.e., the threshold of cleanliness when the cleaning process is implemented).

In addition to having a spraying mechanism for spraying onto reflector 26, other similar arrangements of spraying mechanism can be incorporated for one or more of the optical elements (e.g., reflector, lens, window such as Brewster window, and the like). For example, if both reflectors of the resonant cavity are exposed to the sample gas such that contaminants may foul the surfaces of the reflectors, spraying systems can be affixed in situ to each reflector to remove the contaminants.

Further, the valve or valves that are positioned between the source of carbon dioxide and the spray nozzle can be automatically controlled (e.g., by microprocessors). In this way, when the monitoring system detects an amount of resonating light loss above a threshold level at the optical element, the valve(s) can be actuated such that a burst of spray is emitted from the nozzle to remove the contaminants from the surface of the optical element. For example, in the embodiment shown in FIG. 2., signals from the detector 27 can be transmitted to a controller 45 to control valves 40 and 44 such that a burst of $CO_2$ spray is emitted to clean the reflector 26 when needed. Devices and mechanism for automatically controlling valves based on information collected from a monitoring system are commonly known in the art.

The cleaning system of the present invention is particularly well suited for automatic control. First, the size of the optical elements (e.g., reflectors) are small enough that they can be efficiently cleaned by bursts of $CO_2$ spray without manually adjusting the spray nozzle. This is particularly true in the preferred embodiment wherein the isolated cavity is the resonant cavity of a laser since the resonating laser beam is reflected on a small reflecting area on each reflector only. Second, the light transmitted out of the resonant cavity is particularly suitable for detection to indicate the extent of fouling of the reflector. This is because the reflector (e.g., 26) performs three functions: directly contacting and confining the gases being analyzed, reflecting the laser light, and transmitting light outside the cavity to a detector. By determining the ring-down time of the resonating cavity, the condition of the optical element can be reliably monitored.

As an alternative to the embodiments of gas analysis system described above, other gas analysis systems can be adapted to include the spraying system for cleaning an optical element as disclosed in the present invention. For example, the gas analysis system described in U.S. Pat. No. 5,153,671 (which is incorporated by reference herein) can also include the spraying system similar to that on FIG. 2 such that the optical elements in the gas analysis apparatus can be intermittently cleaned.

Although carbon dioxide is used to illustrate the method and apparatus of the present invention, any other gas that can be sublimated from its solid phase (especially a solid phase that can be obtained by an adiabatic expansion through a nozzle) under ambient condition can be used. Other gases may have state characteristics making them suitable for forming sublimable "snow" similar to carbon dioxide (e.g., ammonia and argon). The choice of the gas is determined by the optical application and the contaminants to be removed and will be obvious to one skilled in the art of phase equilibrium and solubilization.

Instead of depending on the inherent pressure of the liquid under storage to expel the substance through the nozzle to form a spray, an externally supplied stream of gas, such as pressurized air, can be used to force the liquid through the nozzle to form a spray that includes the particulate substance and the externally supplied gas. Systems of incorporating a stream of air to carry a spray of particulate matter are known in the art (e.g., as described in U.S. Pat. No. 5,107,764). A system using argon for making argon "snow" that is carried by a stream of gas nitrogen is disclosed in U.S. Pat. No. 5,062,898. These disclosures are incorporated by reference herein.

The following example is provided to illustrate the effectiveness of the apparatus of the present invention to clean periodically the optical elements that has been fouled by contaminants in sample gases, and to illustrate the operation of a gas analysis apparatus of the present invention.

EXAMPLE

To analyze a breath sample from a patient, e.g., for anesthetic gases, an apparatus shown in FIG. 2 is used. In the sampling mode, a sample gas is drawn through the sample chamber 10. It enters through inlet 16 and exits through exit 20. The sample gas may be from the breathing circuit of a patient connected to an anesthesia machine. An inlet valve 18 and exit valve 22 remain open during sampling mode to permit the flow of gas through the cell. Mirrors 26 and 28 form the ends of an optically resonant cavity so that an intense laser beam reflects between the mirrors. The intense laser beam induces scattered light from the molecules of the sample gas. The scattered light exits a window 31 on the sample cell and is detected by detector 29.

The intensity of the laser beam is determined by measuring the optical radiation that emits through one of the mirrors and reaches detector 27. Because the scattered light is also proportional to the intensity of the laser beam, the scattered light is also an indicator of the laser beam intensity. During the sampling mode, contaminants in the sample gas deposit on the mirrors, causing a diminution of the laser intensity. This is observed directly on the power monitor detector 27 (alternatively, the extent of contamination can be determined by the diminished signals on the scattered light detector 31).

When the laser intensity reaches predetermined threshold (or minimum) value, the system changes to a cleaning mode. The following sequence of events describes the cleaning mode:

0) During sampling mode, valve 44 remains closed and valve 40 remains open. This permits the filling of the plenum 42 with a predetermined volume of the cleaning medium 36 from a larger reservoir 38 of cleaning medium.

1) Valve 18 closes to stop the flow of sample gas into the cell.

2) Valve 40 closes.

3) Valve 44 opens, which causes the rapid discharge of the cleaning medium through the nozzle 34. The rapid expansion through the nozzle causes freezing of the cleaning medium, so that a jet 33 of frozen particles impinges on the surface of the contaminated mirror. The jet directs the flow to a small location on the mirror that is also the location of the resonant laser beam. The jet removes the contaminants from the mirror surface. The particles from the jet quickly sublimate, and the gaseous cleaning medium and contaminants exit the cell through exit 20 and valve 22.

4) Valve 44 closes.

5) Valve 40 opens to recharge the plenum for the next cleaning cycle.

6) Steps 3 through 6 can be repeated as necessary to remove all contaminants on an optical surface, or to cleanse other optical surfaces (e.g. the other mirror).

7) Valve 18 re-opens to permit sample gas to enter the cell, ending the cleaning mode and resuming the sampling mode.

Although the illustrative embodiments of the gas analysis system of the present invention and the method of using the system have been described in detail, it is to be understood that the above-described embodiments can be modified by one skilled in the art, especially in sizes, shapes, and combination of various described features without departing from the spirit and scope of the invention. For example, instead of using a plenum to provide a fixed amount of liquid carbon dioxide, the valves can be controlled to provide a timed duration of spraying.

What is claimed is:

1. A gas analysis apparatus for analyzing breaths, comprising:

a light source for emitting light;

a body having an isolated cavity in which the light emitted by the light source propagates, a breath sample inlet port for the introduction of a breath sample gas into the cavity to be irradiated by the light, and an outlet port for venting gas from the cavity; wherein the cavity encloses one or more optical elements each having a surface;

a detector for analyzing light scattered by the breath sample gas; and a spraying means connected to the body for spraying a sublimable substance on the surface of the one or more optical elements in the cavity in-situ for removing breath contaminants therefrom, said spraying means being adapted to emit repeatable doses of specific amount of the sublimable substance to impinge with sufficient momentum on said surface to remove breath organics-containing contaminants therefrom.

2. The gas analysis apparatus according to claim 1 wherein the spraying means comprises a nozzle located in the cavity, a reservoir of a fluid transformable into a sublimable substance by adiabatic expansion, and a plenum operatively connected and in fluid communication with the reservoir and the nozzle, the plenum being adapted for storing and isolating a dose of a specific amount of the fluid at above-atmospheric pressure such that each time the spraying means is activated a specific amount of the fluid is transferred from the plenum and sprayed from the nozzle as a sublimable substance, such that repeatable doses of specific amount of the sublimable substance can be directed to impinge on said surface.

3. The gas analysis apparatus according to claim 1 wherein the sprayed sublimable substance is particulate.

4. The gas analysis apparatus according to claim 1 wherein the sublimable substance is carbon dioxide.

5. The gas analysis apparatus according to claim 1 wherein the light is generated by a gain medium of a laser and the isolated cavity encompasses a resonating cavity of the laser for amplification of light.

6. The gas analysis apparatus according to claim 5 further having a means for monitoring resonating light loss on the surface of an optical element to automatically activate the spraying means to clean the surface when the resonating light loss is above a threshold level.

7. The gas analysis apparatus according to claim 1 wherein the spraying means is adapted to spray the sublimable substance such that a transient liquid form of the sublimable substance is formed to remove contaminant.

8. A method of analyzing a breath sample gas using a gas analysis apparatus which has a light source for emitting light, a body having an isolated cavity in which the light emitted by the light source propagates, a sample inlet port for the introduction of a breath sample gas into the cavity, an outlet port for venting gas from the cavity wherein the cavity has an optical element having a surface, and a detector for analyzing light scattered by the breath sample gas; the method comprising:

(a) admitting a breath sample gas for analysis into the isolated cavity;

(b) analyzing the breath sample gas by irradiating the breath sample gas with light emitted from the light source and detecting the scattered light; and (c) spraying a sublimable substance on the surface of the optical elements to impinge with sufficient momentum to remove breath organics-containing contaminants from said surface.

9. The method according to claim 8 further comprising monitoring the light loss of light from the light source at the surface of the optical element to determine the time for spraying the sublimable substance.

10. The method according to claim 9 wherein the isolated cavity is a laser resonant cavity and the light loss is monitored by measuring ring-down time in the resonant cavity.

11. The method according to claim 9 wherein monitoring the light loss comprises monitoring the light propagated from isolated cavity.

12. The method according to claim 8 wherein the sublimable substance is carbon dioxide.

13. The method according to claim 8 wherein the sublimable substance is particulate.

14. The method according to claim 8 wherein the sublimable substance is sprayed intermittently in doses of a specific amount.

15. The method according to claim 14 comprising isolating an amount of a fluid of substance to be sprayed to obtain a dose of a specific amount.

16. The method according to claim 8 wherein the step of spraying comprising spraying the sublimable substance such that a transient liquid form of the sublimable substance is formed to remove contaminant.

17. A gas analysis apparatus comprising:

a light source for emitting light;

a body having an isolated cavity in which the light emitted by the light source propagates, a sample inlet port for the introduction of a sample gas into the cavity to be irradiated by the light, and an outlet port for venting gas from the cavity; wherein the cavity encloses one or more optical elements each having a surface;

a detector for analyzing light scattered by the sample gas;

a spraying system connected to the body for spraying a sublimable substance on the surface of the one or more optical elements in the cavity in-situ for removing contaminants therefrom; and a means for monitoring light loss on the surface of one or more of said optical elements to enable activating the spraying system to clean the suffice when the resonating light loss is above a threshold level.

18. A method analyzing a sample gas using a gas analysis apparatus which has a light source for emitting light, a body having an isolated cavity in which the light emitted by the light source propagates, a sample inlet port for the introduction of a sample gas into the cavity, an outlet port for venting gas from the cavity wherein the cavity has an optical element having a surface, and a detector for analyzing light scattered by the gas; the method comprising:

(a) admitting a sample gas for analysis into the isolated cavity;

(b) analyzing the sample gas by irradiating the sample gas with light emitted from the light source and detecting the scattered light;

(c) isolating an amount of a fluid a substance that is sublimable at atmospheric pressure to obtain a dose of a specific amount such that doses or the specific amount can be repeated; and (d) spraying the fluid of the dose of a specific amount to form sublimable substance to impinge on the surface of the optical elements to remove contaminants therefrom.

19. A gas analysis apparatus for analyzing breaths, comprising:

a light source for emitting light;

a body having an isolated cavity in which the light emitted by the light source propagates, a breath sample inlet port for the introduction of a breath sample gas into the cavity to be irradiated by the light, and an outlet port for venting gas from the cavity; wherein the cavity encloses one or more optical elements each having a surface;

a detector for analyzing light scattered by the breath sample gas; and a spraying system connected to the body for spraying a sublimable substance on the surface of the one or more optical elements in the cavity in-situ for removing breath contaminants therefrom, said spraying system being adapted to emit repeatable doses of specific amount of the sublimable substance to impinge with sufficient momentum on said surface to remove breath contaminants therefrom, said spraying system comprising a nozzle located in the cavity, a reservoir of a fluid transformable into a sublimable substance by adiabatic expansion, and a plenum operatively connected and in fluid communication with the reservoir and the nozzle, the plenum being adapted for storing and isolating a dose of a specific amount of the fluid at above-atmospheric pressure such that each time the spraying system is activated a specific amount of the fluid is transferred from the plenum and sprayed from the nozzle as a sublimable substance, such that repeatable doses of specific amount of the sublimable substance can be directed to impinge on said surface, the reservoir and the plenum are adapted to transfer doses of specific amount of liquid from the reservoir to the plenum.

20. A method of analyzing a breath sample gas using a gas analysis apparatus which has a light source for emitting light, a body having an isolated cavity in which the light emitted by the light source propagates, a sample inlet port for the introduction of a breath sample gas into the cavity, an outlet port for venting gas from the cavity wherein the cavity has an optical element having a surface, and a detector for analyzing light scattered by the breath sample gas; the method comprising:

(a) admitting a breath sample gas for analysis into the isolated cavity;

(b) analyzing the breath sample gas by irradiating the breath sample gas with light emitted from the light source and detecting the scattered light;

(c) spraying a sublimable substance on the surface of the optical elements to remove breath contaminants therefrom; and (d) monitoring the resonating light loss at the surface of the optical element to determine the time for spraying the sublimable substance.

* * * * *